(12) United States Patent
Engel et al.

(10) Patent No.: US 7,241,453 B2
(45) Date of Patent: Jul. 10, 2007

(54) ANTIMICROBIAL SURFACES

(75) Inventors: Robert Engel, Carle Place, NY (US); JaimeLee Iolani Cohen, Whitestone, NY (US); Karin Melkonian Fincher, Floral Park, NY (US)

(73) Assignees: Long Island University, Brookville, NY (US); Research Foundation of the City University of New York, New York, NY (US); Pace University, New York, NY (US)

( * ) Notice: Subject to any disclaimer, the term of this patent is extended or adjusted under 35 U.S.C. 154(b) by 672 days.

(21) Appl. No.: 10/117,311

(22) Filed: Apr. 5, 2002

(65) Prior Publication Data

US 2005/0181006 A1 Aug. 18, 2005

(51) Int. Cl.
*A01N 24/34* (2006.01)
(52) U.S. Cl. .................................. 424/402; 424/404
(58) Field of Classification Search ............... 424/443, 424/402, 404, 433

See application file for complete search history.

(56) References Cited

U.S. PATENT DOCUMENTS

| | | | |
|---|---|---|---|
| 5,263,992 A | 11/1993 | Guire | |
| 5,476,509 A | 12/1995 | Keogh et al. | |
| 6,033,719 A | 3/2000 | Keogh | |
| 6,299,604 B1 | 10/2001 | Ragheb et al. | |
| 6,306,454 B1 | 10/2001 | Ung-Chhun et al. | |
| 6,444,415 B1 * | 9/2002 | Tanaka et al. | 430/517 |

FOREIGN PATENT DOCUMENTS

| EP | 514588 | * | 11/1992 |
|---|---|---|---|
| WO | WO-0015897 | * | 3/2000 |

OTHER PUBLICATIONS

Cohen et al, Polycations. IX. Polyammonium Derivatives of Cyclodextrins: Syntheses and Binding to Organic Oxyanions, 2000, Heteroatom Chemistry, vol. 11 No. 7, pp. 546-555.*
Cohen et al, Polycations. IX. Polyammonium derivatives of cyclodextrins: Synthesis and Binding to Organic Oxyanions, Heteroatom chemistry, vol. 11, No. 7, 2000.*
Kim et al., Dye molecules as bridges for functional modifications of nylon: antimicrobial functions, Textile Research Journal, 2000, 70 (8), 728-733.(ABS).*
Fabian, et al., "Polycations: Syntheses of Polyammonium Strings as Antibacterial Agents", *Synlett*, 1997. 1007-1009.
Strekas, et al., "Polycations. 5. Inducement of Ψ-DNA Circular Dichroism Signals for Duplex Deoxyribonucleotide Homopolymers by Polycationic Strings", *Archives of Biochemistry and Biophysics*, 1999. 364(1):129-131.

Cohen, et al., "Polycations. IX. Polyammonium Derivatives of Cyclodextrins: Syntheses and Binding to Organic Oxyanions", *Heteroatom Chemistry*, 2000. 11(7):546-555.
Kanazawa, et al., "Polymeric Phosphonium Salts as a Novel Class of Cationic Biocides. III. Immobilization of Phosphonium Salts by Surface Photografting and Antibacterial Activity of the Surface-Treated Polymer Films", *Journal of Polymer Science: Part A: Polymer Chemistry*, 1993. 31:1467-1472.
Tiller, et al., "Designing Surfaces that Kill Bacteria on contact", *PNAS*, 2001. 98(11):5981-5985.
A.J. Isquith, E.A. Abbott, and P.A. Walters, "Surface-Bonded Antimicrobial Activity of an Organosilicon Quaternary Ammonium Chloride", *Applied Microbiology*, vol. 24, pp. 859-863 (1973).
Wendy E. Krause, "A Universal Technique for Antimicrobial Surface Preparation Using Quaternary Ammonium-Functionalized Dendrimers", ABSTRACT *National Center For Environmental Research* at http://es.epa.gov/ncer_abstracts/sbir/02/phase1/pollution/krause.html.

* cited by examiner

*Primary Examiner*—Alton Pryor
(74) *Attorney, Agent, or Firm*—Hoffmann & Baron, LLP; Irving N. Feit

(57) ABSTRACT

These and other objectives will be apparent to those having ordinary skill in the art have been achieved by providing an antimicrobial surface having formula 1:

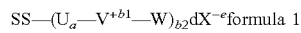

$$SS-(U_a-V^{+b1}-W)_{b2}dX^{-e} \text{ formula 1}$$

wherein:
SS represents a modified solid surface that comprises a hydroxyl group in the unmodified state thereof;
a represents 0 or 1;
U represents $-Y^1T-$;
$Y^1$ represents $-O-$, $-S-$, or $-NQ-$;
Q represents H; a saturated or unsaturated hydrocarbon group having 1-24 atoms; phenyl; or benzyl;
T represents a saturated or unsaturated hydrocarbon chain having 1-24 atoms;
V represents a positively charged moiety;
b1 represents 1 or 2;
b2 represents 1-3;
W represents LZ;
L represents a saturated or unsaturated hydrocarbon chain having 10-24 atoms;
Z represents $-H$, $-OH$, $-SH$, $-F$, $-Cl$, $-Br$, $-I$, $-OR$, $-HN(O)CQ$, or $-O(O)CQ$;
R represents a saturated or unsaturated hydrocarbon group having 1-24 carbon atoms; phenyl; or benzyl;
X represents an anion;
d represents 1 or 2; and
e represents 1-3;
wherein b1×b2=d×e.

29 Claims, No Drawings

ANTIMICROBIAL SURFACES

BACKGROUND OF THE INVENTION

Current fears of antibiotic-resistant bacteria and other microbes as well as of bioterrorism have increased the importance of developing new ways to protect people from microbial infection. It is, for example, important to develop new materials for making clothing that can be more safely worn in contaminated environments. Such materials would be useful, for example, in hospitals and during military and civilian operations where bacterial contamination has occurred, or is expected.

In developing new antimicrobial materials, it is important to discourage further antibiotic resistance. Ideally, therefore, novel antimicrobial materials will function through non-specific, non-metabolic mechanisms.

For example, polycationic (quaternary ammonium) strings developed in the laboratory of Robert Engel are reported to have antibacterial activity. See Fabian et al, Syn. Lett., 1007 (1997); Strekas et al, Arch. Biochem. and Biophys. 364, 129-131 (1999); and Cohen et al, Heteroat. Chem. 11, 546-555 (2000). No suggestion has been made, however, to attach these molecules to surfaces to render the surfaces antimicrobial. Nor have there been any reports regarding which of these molecules would be most effective when attached to surfaces.

Suggestions have been made to attach other antibiotic agents, such as gentamycin and penicillin, to the surface of medical devices. See, for example, Keogh et al. U.S. Pat. No. 5,476,509, Ung-Chhun et al, U.S. Pat. No. 6,306,454, Keogh, U.S. Pat. No. 6,033,719, Ragheb et al, U.S. Pat. No. 6,299,604, and Guire, U.S. Pat. No. 5,263,992. See also Kanazawa et al., Polym. Sci., Part A-I 31, 1467-1472 (1993).

There is, clearly, a need for new materials having antimicrobial agents stably attached to their surfaces. Ideally, the antimicrobial agents do not lead to resistance, and are not detached from their surfaces when the material is washed. It is particularly desirable to develop such materials suitable for use in making clothing. Especially needed is microbe-resistant clothing made of carbohydrate and/or protein based materials, such as cotton, wool and silk as well as blends thereof. It is further desirable to develop other types of antimicrobial surfaces, such as paper and wood surfaces.

SUMMARY OF THE INVENTION

These and other objectives will be apparent to those having ordinary skill in the art have been achieved by providing an antimicrobial surface having formula 1:

$$SS-(U_a-V^{+b1}-W)_{b2}dX^{-e} \qquad \text{formula 1}$$

wherein:

SS represents a modified solid surface that comprises a hydroxyl group in the unmodified state thereof;

a represents 0 or 1;

U represents —Y T-;

$Y^1$ represents —O—, —S—, —NQ- or —SiR$_2$—;

Q represents H; a saturated or unsaturated hydrocarbon group having 1-24 atoms; phenyl; or benzyl;

R represents a saturated or unsaturated hydrocarbon group having 1-24 carbon atoms; phenyl; or benzyl;

T represents a saturated or unsaturated hydrocarbon chain having 1-24 atoms;

V represents a positively charged moiety;

b1 represents 1 or 2;

b2 represents 1-3;

W represents LZ;

L represents a saturated or unsaturated hydrocarbon chain having 10-24 atoms;

Z represents —H, —OH, —SH, —F, —Cl, —Br, —I, —OR, —HN(O)CQ, or —O(O)CQ;

X represents an anion;

d represents 1 or 2; and e represents 1-3;

wherein b1×b2=d×e.

In another embodiment, the invention relates to a method for increasing the resistance to microbial growth of a material having on its surface (SS) a hydroxyl group covalently bonded to a carbon or a silicon atom, the method comprising converting the surface to the antimicrobial surface described above.

DETAILED DESCRIPTION OF THE INVENTION

The invention relates to novel antimicrobial surfaces of solid materials. The materials are suitable for manufacturing objects, such as clothing, bandages, sutures, protective gear, containers, and the like.

The antimicrobial surface has the structure:  SS—(U$^a$—V$^{+b1}$—W)$_{b2}$dX$^{-e}$ (formula 1). In formula 1, SS represents a solid surface that has been modified by covalent attachment of the —(U$_a$—V$^{+b1}$—W)— moiety. In its unmodified state, the solid surface comprises a hydroxyl group attached to a carbon or silicon atom.

When the hydroxyl group is attached to a carbon atom in the unmodified solid surface, the surface will generally comprise carbohydrates, proteins, or mixtures thereof.

In this specification, carbohydrates refer to all polymers of (+)-glucose. Although carbohydrates include starch and glycogen, the carbohydrate of primary interest in the present specification is cellulose. The cellulose may, for example, be in the form of bulk cellulose, or in the form of cotton, linen, rayon, or cellulose acetate. The cotton may, for example, be cotton cloth, cotton gauze or bulk cotton. The carbohydrates may also be in the form of wood or paper.

Other types of material wherein a surface hydroxyl group is attached to a carbon atom include proteinacious materials. Materials comprising proteins include wool and silk.

Each of the materials described above may exist by itself, or as blends with one or more other materials. For example, any of the forms of cellulose described above may be blended with other forms of cellulose. Similarly, any of the forms of proteinacious materials described above may be blended with other forms of proteinacious materials. Moreover, any of the forms of cellulose described above may be blended with any of the forms of proteinacious materials described above. For example, wool and silk may be blended with cotton. Also, any of the materials and blends described above may be blended with other natural or synthetic materials, such as nylon and polyesters. The materials may, for example, be fabrics for making clothing or protective garments.

When the hydroxyl group is attached to a silicon atom on the solid surface, the material comprising the solid surface is typically silica, e.g. glass. The glass modified in accordance with the present invention may, for example, be part of a medical instrument.

In describing the modified surfaces represented by formula 1, various chemical moieties will be defined as hydrocarbon groups or hydrocarbon chains. As used in this specification, a hydrocarbon group is bonded at one end to another chemical moiety. A hydrocarbon chain is bonded at each end to another chemical moiety, e.g. independently, to a hydrocarbon group or to an atom.

The hydrocarbon chains or groups in formula 1 are unbranched, and have the number of atoms specified. The hydrocarbon chain may be saturated or unsaturated, and may or may not comprise one or more heteroatoms (i.e. O, S, or NH). From ⅔ to all of the atoms in the hydrocarbon chain or group are saturated or unsaturated carbon atoms. From none to ⅓ of the atoms in the chain or group are heteroatoms.

Saturated hydrocarbon chains may comprise methylene units. There may be 1-24 methylene groups in a saturated hydrocarbon chain, unless stated otherwise.

Saturated hydrocarbon chains may also comprise epoxy units, herein designated —$(CH_2(O)CH_2)_{m2}$—, wherein m2 represents 1-12, unless stated otherwise, and —$(CH_2(O)CH_2)$— represents:

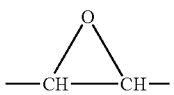

The unsaturated hydrocarbon chains or groups may contain a mixture of saturated and unsaturated carbon atoms. Alternatively, the unsaturated hydrocarbon chains or groups may contain only unsaturated carbon atoms. Thus, the unsaturated hydrocarbon chains or groups may contain one or more double and/or triple bonds. There may be 2-24 carbon atoms in an unsaturated hydrocarbon chain or group.

Some examples of $C_1$-$C_8$ hydrocarbon groups that contain no heteroatoms include methyl, ethyl, propyl, propenyl, butyl, 1- or 2-butynyl, 1-, 2-, or 3-pentenyl, hexyl, heptyl and octyl. Some examples of saturated $C_{10}$-$C_{24}$ hydrocarbon groups that contain no heteroatoms include decyl, dodecyl, tetradecyl, hexadecyl, and octadecyl. Some examples of unsaturated $C_{10}$-$C_{24}$ hydrocarbon groups that contain no heteroatoms include oleyl, linoleyl, and linolenyl, especially cis-oleyl, cis, cis-linoleyl, and cis, cis, cis-linolenyl. The corresponding chains lack a hydrogen atom at the distal end, i.e. at the ω position, of the group.

Hydrocarbon chains that have heteroatoms include, for example, —$(CH_2CH_2Y^2)_{m1}$—, wherein m1 represents 1-8, and $Y^2$ represents O, S, or NH.

The hydrocarbon chains or groups may be mixtures of any of the chains and groups described above. The mixtures may, for example, contain only saturated hydrocarbon chains or groups, only unsaturated hydrocarbon chains or groups, or a mixture of saturated and unsaturated hydrocarbon chains or groups. As mentioned above, any of the hydrogen chains or groups may contain one or more heteroatoms.

Also in this specification, the phenyl ring of a phenyl and/or benzyl group may be unsubstituted, or may be substituted with any substituent capable of stably substituting a phenyl ring. Some examples of suitable substituents include —H, —OH, —SH, —F, —Cl, —Br, —I, —OR, —NH2, —NHR, —NHR2, —HN(O)CR, or —O(O)CR, wherein R represents H, a saturated or unsaturated hydrocarbon group having 1-24 carbon atoms, phenyl, or benzyl. Preferably, the hydrocarbon chain has 1-3 carbon atoms, preferably 1-3 saturated carbon atoms, i.e. methyl, ethyl, propyl, or isopropyl. The phenyl and benzyl groups are not substituted with more than one additional phenyl or benzyl group, and are preferably not substituted with any additional phenyl or benzyl groups.

The group U in formula 1 is an optional linker. When U is present (i.e. a=1), U separates the solid surface (SS) and the positively charged group (V). When the group U is absent (i.e. a=0), the solid surface SS is bonded directly to the charged moiety V.

For stability, the linking group U is preferably present (i.e. a=1) when the hydroxyl group on the unmodified solid surface is attached to a silicon atom, as, for example, in the case of silica, e.g. glass. Modified silica surfaces are more stable when the positively charged moiety, V in formula 1, is bonded to a carbon atom then when V is bonded to a silicon atom. The carbon atom, e.g., a hydrocarbon chain, in turn, is covalently bonded to the oxygen atom of the hydroxyl group on the surface of the silica.

The group U in formula 1 represents —$Y^1T$-. $Y^1$ may, for example, represent —O—, —S—, —NQ- or —$SiR_2$—. R represents a saturated or unsaturated hydrocarbon group having 1-24 atoms, phenyl, or benzyl. Q represents a hydrogen atom or R. Preferably, Q represents hydrogen, methyl, or ethyl. Preferably, R represents methyl or ethyl.

T represents a saturated or unsaturated hydrocarbon chain having 1-24 atoms. Preferably, T represents a saturated alkyl chain having no heteroatoms. The saturated alkyl chain preferably has 1-3 carbon atoms.

V in formula 1 represents a positively charged moiety. The positively charged moiety may, for example, be a singly or a doubly charged moiety. In a singly charged moiety, b1 in formula 1 represents 1. In a doubly charged moiety, b1 represents 2. The singly or doubly charged moiety may, for example, comprise one or two positively charged nitrogen atoms, one or two positively charged phosphorous atoms, or one or two positively charged sulfur atoms.

In one embodiment, the positively charged moiety comprises a singly charged quaternary ammonium, quaternary phosphonium or sulfonium group, having the formula $^+$—$NR_2$—, $^+$—$PR_2$—, or $^+$—$SR$, respectively, wherein R is as defined above. In the quaternary ammonium and phosphonium ions, the two R groups on the N or P atom may be the same, or different. Preferably, both R groups represent methyl or ethyl. The positively charged nitrogen, phosphorous and sulfur atoms are also covalently bonded to SS—$U_a$ and to W. See formula 1.

In a preferred embodiment, positively charged moiety V comprises two positively charged nitrogen atoms, such as, for example, —$^+NR_2$— T-$NR_2^+$— or 1,4-diazoniabicyclo [2.2.2]octane. In another embodiment, V comprises two positively charged sulfur atoms, such as, for example, —$^+SR$-T-$SR^+$— or 1,4-dithioniumcyclohexane. In this embodiment, T represents a saturated or unsaturated hydrocarbon chain having 1-24 atoms. Preferably, T represents a saturated alkyl chain having no heteroatoms. The saturated alkyl chain preferably has 1-3 carbon atoms.

The moiety W in formula 1 represents LZ. L represents a saturated or unsaturated hydrocarbon chain. The minimum number of atoms in the chain is 10, preferably 12, and more preferably 14. The maximum number of atoms in the chain is 24, preferably 18. The optimum number of atoms in the chain is 16.

Hydrocarbon chains L that have heteroatoms include, for example, —$(CH_2CH_2Y^2)_{m1}$—, wherein m1 represents 4-8, and $Y^2$ is as described above. Another possible hydrocarbon chain is —$(CH_2(O)CH_2)_{m2}$—, wherein m2 represents 5-12; and —$(CH_2(O)CH_2)$— is as described above.

The chains preferably contain no heteroatoms. More preferably, the chains contain only saturated carbon atoms.

L may represent hydrocarbon chains that all have the same length. Preferably, all of the hydrocarbon chains L have 12-18 atoms, preferably 14-16 atoms, more preferably 16 atoms, most preferably 16 carbon atoms, and optimally 16 saturated carbon atoms.

Alternatively, L may represent a mixture of hydrocarbon chains. Preferably, at least some of the hydrocarbon chains L in the mixture have 12-18 atoms, preferably 14-16 atoms, more preferably 16 atoms, most preferably 16 carbon atoms, and optimally 16 saturated carbon atoms.

It is especially desirable for a significant number of hydrocarbon chains L to have 16 atoms. Generally, at least about 10%, preferably at least about 25%, more preferably at least about 50%, most preferably at least about 75%, and optimally at least about 90% of the hydrocarbon chains L in the mixture have 16 atoms, preferably 16 carbon atoms, and more preferably 16 saturated carbon atoms.

Z represents a stable chemical moiety at an end of hydrocarbon chain L. Z may represent, for example, —H, —OH, —SH, —F, —Cl, —Br, —I, —OR, —$NH_2$, —NHR, —$NR_2$, —HN(O)CQ (amido group), or —O(O)CQ (ester group), wherein R and Q are defined as above. The preferred R and Q groups are methyl and ethyl. Z preferably represents H. The preferred moieties W are dodecyl, tetradecyl, hexadecyl, and mixtures thereof.

X represents an anion that balances the charge of positively charged moiety V. The anion may be singly charged, in which case e in formula 1 is 1, doubly charged, in which case e in formula 1 is 2, or triply charged, in which case e in formula 1 is 3. Some examples of suitable anions include halide (fluoride, chloride, bromide, or iodide), nitrate, sulfate, bisulfate, phosphate (mono-, bi-, or triphosphate), carbonate, bicarbonate, or acetate.

The numbers represented by b2 and d are such that the overall charge is neutral, i.e. b1×b2=d×e.

Antimicrobial Activity

The materials that have been subjected to surface modification according to the invention demonstrate excellent antimicrobial properties. In this specification, antimicrobial properties refer to the ability to resist growth of single cell organisms, e.g. bacteria, fungi, algae, and yeast, as well as mold.

The bacteria include both gram positive and gram negative bacteria. Some examples of Gram positive bacteria include, for example, *Bacillus cereus*, *Micrococcus luteus*, and *Staphylococus aureus*. Some examples of Gram negative bacteria include, for example, *Escherichia coli*, *Enterobacter aerogenes*, *Enterobacter cloacae*, and *Proteus vulgaris*. Strains of yeast include, for example, *Saccharomyces cerevisiae*.

In order to demonstrate the antimicrobial properties achieved in accordance with the invention, surfaces (SS) were modified and tested for antimicrobial activity. Briefly, carbohydrate-based surfaces (100% cotton cloth, commercial grade; Whatman Grade 1 Chr) were activated for attachment of a cationic ligand by treatment with an excess of p-toluenesulfonyl chloride in pyridine solution, followed by washing with water chilled with ice. The activated cotton was placed in an acetonitrile solution containing an excess of 1-aza-4-(fatty alkyl)azoniabicyclo[2.2.2]octane, and agitated for 24 hours. Cotton modified with ligands having the following fatty alkyl groups were produced and tested:
  octyl (C8)
  decyl (C10)
  dodecyl (C12)
  hexadecyl (C16)
  octadecyl (C18)

The medium used for bacterial growth was prepared from Bacto-tryptone, Bacto-agar, yeast extract and sodium chloride. Each modified surface sample was investigated for its antibacterial effect with each of the bacteria studied in a four-part experiment. Specifically, on the same plate bearing the growth medium were placed four separate experimental runs, those being:
  A—untreated surface material, to which no bacteria had been added
  B—surface material that had been subjected to the solvent washing procedures of reaction but without addition of the reagent materials, to which the bacteria being investigated were added
  C—untreated surface material, to which the bacteria being investigated were added
  D—modified surface material, to which the bacteria being investigated were added.

The growth plate holding the four experiments was incubated overnight at 35° C. Growth was noted visually in the region around the material surface. Subsequently, the material was removed from the growth medium and placed in 4 mL of fresh growth medium and incubated at 35° C. for 16 hr. Growth of bacteria was measured turbidimetrically using a Beckman Model 25 UV/VIS spectrophotometer.

Seven bacterial strains (four Gram negative and three Gram positive) were investigated, as noted below.

In all instances, experiments A, B and C exhibited full growth of the bacteria in the initial growth studies. Bacterial growth on the modified surface and in the surrounding region, experiment D, was noted to be completely absent only in the sets of bacteria/modified surface noted below. Further, continued growth as measured turbidimetrically was noted to be zero as well for each of these systems:
  *Escherichia coli* (ATCC #14948)—C16
  *Enterobacter aerogenes* (ATCC #13048)—C16
  *Enterobacter cloacae* (ATCC #13047)—C12, C16
  *Proteus vulgaris* (ATCC #13315)—C12, C16, C18
  *Bacillus cereus* (ATCC #14579)—C10, C12, C16, C18
  *Micrococcus luteus* (ATCC #9341)—C10, C12, C16, C18
  *Staphylococcus aureus* (ATCC #6538)—C10, C12, C16, C18

The results shown above demonstrate that broad antibacterial activity can be imparted to carbohydrate surfaces through the covalent attachment of cationic agents with lipophilic groups. The activity is apparent for a large number of different types of microorganisms.

The specificity is remarkable. Surfaces modified with C8 exhibited minimal (if any) antibacterial activity. Clearly, the presence of a sufficiently long (at least ten atoms) lipophilic chain attached to the surface cationic site is required for activity.

Only C16 demonstrated activity against all seven bacterial strains tested. Therefore, optimal antibacterial activity is observed toward both Gram negative and Gram positive bacteria with a chain length of 16 carbons in the lipophilic portion.

While the inventors do not wish to be bound by any theory, the antibacterial activity may be understood as occurring in a stepwise manner. The lipophilic chains may be subsumed by the bacterial species to a stage where the cationic portion is brought into intimate contact with the cell surface, and is subsumed sufficiently far that it is not easily expelled. Detergent-like action then results in cell surface disruption initiating cell destruction.

A particular advantage of such action is the lack of consumption of the antibacterial agent. The antibacterial agent is not changed in the process and remains attached to the surface. Moreover, the antibacterial activity is non-specific and non-metabolic. Therefore, the danger of encouraging resistant strains of bacteria is reduced.

Modification of Surfaces

Activation of Hydroxyl Groups

Surfaces can be modified in accordance with the invention by methods known in the art. In the case of surfaces that have hydroxyl groups attached to carbon atoms, for example, carbohydrate and protein surfaces, activation of surface hydroxyl groups may be accomplished by converting the hydroxyl group to an active ester linkage.

Hydroxyl groups may be converted to an active ester linkage by reacting the hydroxyl groups with a reagent in a suitable medium. The reagent may, for example, include benzenesulfonyl chloride, p-toluenesulfonyl chloride, thionyl chloride, and phosphorus tribromide. Suitable media for the reaction include, but are not limited to, pyridine, hexane, heptane, ether, toluene, ethyl acetate, and mixtures thereof. The amount of reagent and volume of suitable medium are known to those in the art.

It is not necessary to activate all of the available hydroxyl sites present on the surface of a material. For example, less than about 10% of the available hydroxyl groups on a surface may be activated to subsequently provide sufficient antimicrobial activity. Preferably, about 25% of the available hydroxyl groups may be activate, more preferably about 50%, and most preferably about 75% of the available hydroxyl groups may be activated.

Equation 1 below depicts an example of the activation of hydroxyl groups on a carbohydrate by reaction with p-toluenesulfonyl chloride:

Equation 1

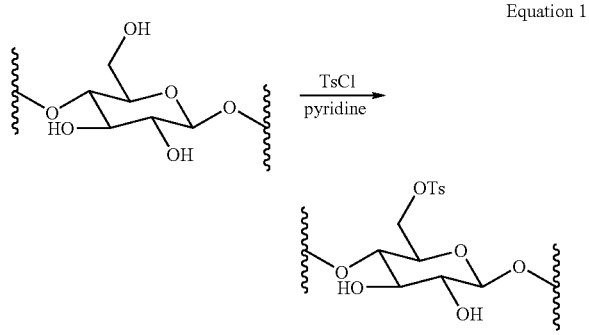

The activation reaction requires a proton-sink. When pyridine is used as the medium, pyridine functions as its own proton-sink. The use of pyridine may be avoided, for example, by using one of the other, inert solvent systems disclosed above, and adding an alkaline compound, such as an insoluble polymeric tertiary amine, to act as the proton-sink. The insoluble polymeric tertiary amine, may be, for example, DEAE-cellulose.

Hydroxyl groups attached to silicon atoms can be modified in the same way as chromatographic media, as is known in the art. For example, such hydroxyl groups may be treated with various substituted halosilanes, such as chlorosilanes or bromosilanes, in a non-reactive (i.e., non-hydroxylic, non-acidic) solvent. The halosilane may have the following structure:

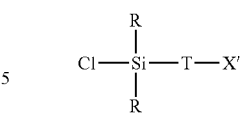

where X' is Cl, Br, or I, and T and R are as described above.

Treatment of the hydroxyl group with, for example, chlorosilane results in binding of the Si atom to the oxygen of the surface hydroxyl group, thus liberating HCl. This reaction provides a linker which can be used for the attachment of a positively charged moiety.

Equation 2 below depicts an example of the activation of hydroxyl groups on silica with a chlorosilane:

Equation 2

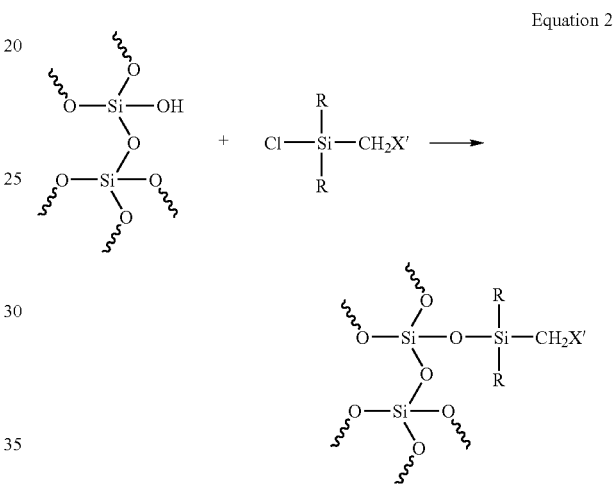

Examples of non-reactive solvents for use in activation of hydroxyl groups on silica surfaces, include, but are not limited to, solvents such as ether, a hydrocarbon, an ester, e.g. ethyl acetate and a simple nitrile, e.g. acetonitrile.

Attachment of Positively Charged Moiety (V)

The surfaces (e.g., carbohydrate, protein, and silica) activated by the process described above are rendered antimicrobial by the chemical attachment of a suitable tertiary amine, thioether, or tertiary phosphine species in a suitable reaction medium. Some examples of suitable reaction media include, acetonitrile, ethanol, methanol, 2-propanol, propionitrile, and mixtures thereof. Examples of tertiary amine, tertiary phosphine, and thioether species useful in the present invention include:

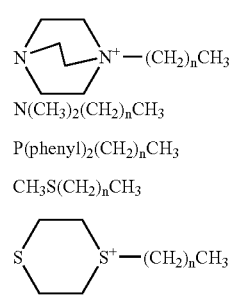

$N(CH_3)_2(CH_2)_nCH_3$ $P(phenyl)_2(CH_2)_nCH_3$ $CH_3S(CH_2)_nCH_3$ wherein n is 9 to 23.

An example of the attachment of a positively charged moiety, 4-hexadecyl-1-aza-4-azoniabicyclo[2.2.2]octane to an active group on a carbohydrate is shown in equation 3 below:

Equation 3

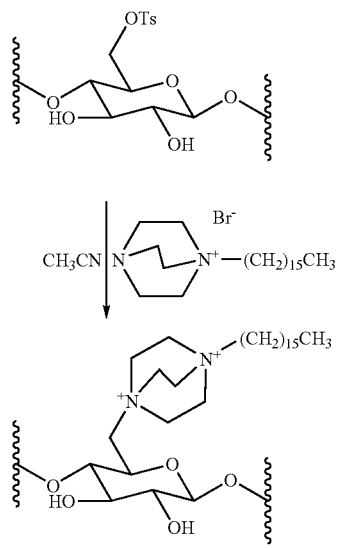

An example of the attachment of a positively charged moiety, 1-aza-4-(tetradecyl)azonia-[2,2,2]-bicyclooctane to an active group on silica is shown in equation 4 below, wherein R, X, and X' are as described above:

Equation 4

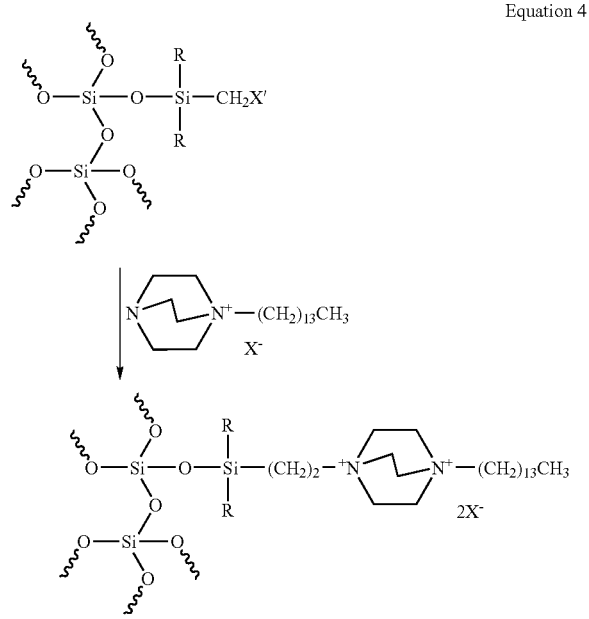

Once the modification of a antimicrobial surface is complete, the prepared surface may be sequentially washed with a solvent used for the final reaction (e.g., reaction medium used in attachment of positively charged moiety), brine and water, and then dried.

EXAMPLES

Example 1

Preparation of N-hexadecyl-N,N-dimethyl-N-(2-thiomethyl)ethylammonium bromide

The ammonium salt N-hexadecyl-N,N-dimethyl-N-(2-thiomethyl)ethylammoniumbromide is prepared by adding 66.1 g (0.210 mol) of 1-bromohexadecane in 150 ml of ethyl acetate to 25 g (0.210 mol) of N,N-dimethyl-N-(2-thiomethyl)ethyl amine in 250 ml of ethyl acetate. The solution mixture is stirred. The resultant precipitate is collected by suction filtration and washed with ether and dried under vacuum.

Example 2

Preparation of Antimicrobial Cotton Cloth with N-hexadecyl-N,N-dimethyl-N-(2-thiomethyl)ethylammonium bromide A 25 g sample of 100% cotton cloth is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed with N-hexadecyl-N, N-dimethyl-N-(2-thiomethyl)ethylammonium bromide (62.4 g, 0.155 mol) in acetonitrile and is agitated overnight. The modified cotton cloth is then removed from the reaction mixture, washed sequentially with acetonitrile, brine and water, and dried in air.

Example 3

Preparation of Antimicrobial Cotton Cloth with 4-hexadecyl-1-aza-4-azoniabicyclo[2.2.2]octane chloride A 25 g sample of 100% cotton cloth (bearing a maximum of 0.465 equivalents of hydroxyl groups, approximately 0.155 equivalents of which are primary hydroxyl groups) is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed in acetonitrile containing 57.74 g (0.155 mol) of 4-hexadecyl-1-aza-4-azoniabicyclo[2.2.2]octane chloride and the reaction mixture is agitated overnight. The modified cotton cloth is then removed from the reaction medium, washed sequentially with acetonitrile, brine and water, and dried in air.

Example 4

Preparation of Antimicrobial Wood

A 25 g sample of wood (maple) (bearing a maximum of 0.465 equivalents of hydroxyl groups, approximately 0.155 equivalents of which are primary hydroxyl groups) is placed in a solution of 29.5 g of the activating agent p-toluenesulfonyl chloride (0.155 mol) in 150 ml pyridine as dispersing medium. The reaction medium is agitated overnight. The modified wood is removed and washed with ice-water. The washed modified wood is then placed in acetonitrile containing 53.40 g (0.155 mol) of 4-tetradecyl-1-aza-4-azoniabicyclo[2.2.2]octane chloride and the reaction mixture was agitated overnight. The modified wood is then removed from the reaction medium, washed sequentially with acetonitrile, brine and water and dried in air.

Example 5

Preparation of Antimicrobial Silk

A 25 g sample of 100% silk (bearing a maximum of 0.057 equivalents of primary hydroxyl groups) is placed in a solution of 10.8 g of the activating agent p-toluenesulfonyl chloride (0.155 mol) in 150 ml pyridine as dispersing medium. The reaction medium is agitated overnight. The modified silk is removed and washed with ice-water. The washed modified silk is then placed in a solution of 21.2 g of 4-hexadecyl-1-aza-4-azoniabicyclo[2.2.2]octane chloride in 100 ml of acetonitrile and the reaction mixture is agitated overnight. The modified silk is then removed from the reaction medium, washed sequentially with acetonitrile, brine and water and dried in air.

Example 6

Preparation of Antimicrobial Wool with 4-hexadecyl-1-aza-4-azoniabicyclo[2.2.2]octane chloride A 25 g sample of 100% wool (bearing a maximum of 0.052 equivalents of hydroxyl groups) is placed in a solution of 9.90 g of the activating agent p-toluenesulfonyl chloride (0.155 mol) in 150 ml pyridine as dispersing medium. The reaction medium is agitated overnight. The modified wool is removed and washed with ice-water. The washed modified wool is then placed in a solution of 20.82 g (0.052 mol) of 4-hexadecyl-1-aza-4-azoniabicyclo[2.2.2]octane chloride in 100 ml of acetonitrile and the reaction mixture is agitated overnight. The modified wool is then removed from the reaction medium, washed sequentially with acetonitrile, brine and water and dried in air.

Example 7

Preparation of Antimicrobial Wool with P-hexadecyl-P,P-diphenylphosphine

A 25 g sample of 100% wool (bearing a maximum of 0.052 equivalents of hydroxyl groups) is placed in a solution of 9.90 g of the activating agent p-toluenesulfonyl chloride (0.155 mol) in 150 ml pyridine as dispersing medium. The reaction medium is agitated overnight. The modified wool is removed and washed with ice-water. The washed modified wool is then placed in a solution of 13.62 g (0.052 mol) of P-hexadecyl-P,P-diphenylphosphine in 100 ml of acetonitrile and the reaction mixture is agitated overnight. The modified wool is then removed from the reaction medium, washed sequentially with acetonitrile, brine and water and dried in air.

Example 8

Preparation of 1'-hexadecyl-1-thionium-4-thiacyclohexane bromide

The sulfonium salt 1-hexadecyl-1-thionium-4-thiacyclohexane bromide is prepared by adding 63.3 g (0.201 mol) of 1-bromohexadecane in 150 ml of ethyl acetate to 25 g (0.201 mol) of 1,4-dithiane in 250 ml of ethyl acetate. The solution mixture is stirred. The resultant precipitate is collected by suction filtration and washed with ether and dried under vacuum.

Example 9

Preparation of Antimicrobial Cotton Cloth with 1-hexadecyl-1-thionium-4-thiacyclohexane bromide A 25 g sample of 100% cotton cloth is placed in a solution of 29.5 g of the activating agent p-toluenesulfonyl chloride (0.155 mol) in 150 ml pyridine as dispersing medium. The reaction medium is agitated overnight. The modified cotton cloth is removed and washed with ice-water. The washed modified cotton cloth is then placed in acetonitrile with 1-hexadecyl-1-thionium-4-thiacyclohexane bromide (62.4 g, 0.155 mol) and is agitated overnight. The modified cotton cloth is then removed from the reaction mixture, washed sequentially with acetonitrile, brine and water, and dried in air.

We claim:

1. An antimicrobial surface having the formula

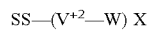

$$SS-(V^{+2}-W)\,X$$

wherein:

SS represents a solid surface of fabric, said solid surface comprising hydroxyl groups in the unmodified state thereof;

$V^{+2}$ represents 1,4-diazoniabicyclo[2.2.2]octane;

W represents a saturated or unsaturated straight-chain hydrocarbon having 10-24 carbon atoms; and X represents an anion that balances the charge of V.

2. An antimicrobial surface according to claim 1, wherein the hydroxyl group is attached to a carbon atom on the solid surface.

3. An antimicrobial surface according to claim 1, wherein W has 10-18 carbon atoms.

4. An antimicrobial surface according to claim 1, wherein W represents a saturated straight-chain hydrocarbon.

5. An antimicrobial surface according to claim 1, wherein the hydrocarbon comprises at least one double bond.

6. An antimicrobial surface according to claim 1, wherein the hydrocarbon comprises at least one triple bond.

7. An antimicrobial surface according to claim 1, wherein X represents a halide, nitrate, sulfate, phosphate, or carbonate.

8. An antimicrobial surface according to claim 1, wherein W has a minimum of 12 carbon atoms.

9. An antimicrobial surface according to claim 1, wherein the solid surface is a surface of clothing.

10. An antimicrobial surface according to claim 1, wherein the solid surface is a surface of a protective garment.

11. An antimicrobial surface according to claim 2, wherein the solid surface comprises a carbohydrate.

12. An antimicrobial surface according to claim 11, wherein the carbohydrate is bulk carbohydrate.

13. An antimicrobial surface according to claim 11, wherein the carbohydrate is cellulose.

14. An antimicrobial surface according to claim 13, wherein the cellulose is bulk cellulose.

15. An antimicrobial surface according to claim 13, wherein the cellulose is cellulose acetate.

16. An antimicrobial surface according to claim 11, wherein the carbohydrate is cotton.

17. An antimicrobial surface according to claim 16, wherein the cotton is cotton cloth, cotton gauze, or bulk cotton.

18. An antimicrobial surface according to claim 17, wherein the cotton cloth is blended with other fabrics.

19. An antimicrobial surface according to claim 2, wherein the solid surface comprises a protein.

20. An antimicrobial surface according to claim 19, wherein the protein is wool.

21. An antimicrobial surface according to claim 19, wherein the protein is silk.

22. An antimicrobial surface according to claim 2, wherein the solid surface is a surface of a garment.

23. An antimicrobial surface according to claim 8, wherein W has 12-16 carbon atoms.

24. An antimicrobial surface according to claim 23, wherein W has 14-16 carbon atoms.

25. An antimicrobial surface according to claim 24, wherein W has 16 carbon atoms.

26. An antimicrobial surface according to claim 4, wherein W has 10-18 carbon atoms.

27. An antimicrobial surface according to claim 4, wherein W has 12-16 carbon atoms.

28. An antimicrobial surface according to claim 4, wherein W has 14-16 carbon atoms.

29. An antimicrobial surface according to claim 4, wherein W has 16 carbon atoms.

* * * * *